(12) United States Patent
Sly

(10) Patent No.: US 7,115,667 B2
(45) Date of Patent: Oct. 3, 2006

(54) OPHTHALMIC FLUID

(75) Inventor: Anthony William Sly, Westminster Perth, WA (US)

(73) Assignee: Planned Products Pty Ltd., Westminster (AU)

( * ) Notice: Subject to any disclaimer, the term of this patent is extended or adjusted under 35 U.S.C. 154(b) by 0 days.

(21) Appl. No.: 10/781,179

(22) Filed: Feb. 18, 2004

(65) Prior Publication Data

US 2004/0167218 A1    Aug. 26, 2004

Related U.S. Application Data

(63) Continuation of application No. 10/049,784, filed as application No. PCT/AU00/00977 on Aug. 16, 2000, now abandoned.

(30) Foreign Application Priority Data

Aug. 18, 1999  (AU) .................... PQ2281

(51) Int. Cl.
*A61K 47/30* (2006.01)
(52) U.S. Cl. .............. 514/786; 514/912; 514/915
(58) Field of Classification Search ............ 514/786, 514/912, 915; 424/78.04
See application file for complete search history.

(56) References Cited

U.S. PATENT DOCUMENTS 4,259,202 A   3/1981  Tanaka et al.
5,981,607 A   11/1999 Ding et al.

FOREIGN PATENT DOCUMENTS

| WO | PCT/US93/00044 | 1/1993 |
| WO | PCT/US95/06302 | 5/1995 |
| WO | PCT/EP96/00697 | 2/1996 |
| WO | WO 98 16217 | 4/1998 |

OTHER PUBLICATIONS

Harvey, et al., "Identification by Combined Gas Chromatography—Mass Spectrometry of Constituent Long—Chain Fatty Acids and Alcohols from the Meibomian Glands of the Rat and a Comparison with Human Meibomian Lipids", *Journal of Chromatography*, pp. 253-263 (1987).
Medline Abstract No. 952309493; J Phar Pharmacol Dec. 1994;46(12):p. 986-93.
Medline Abstract No. 91172507; 1: Ophthalmologica 1990:201(4):206-12.

*Primary Examiner*—Zohreh Fay
(74) *Attorney, Agent, or Firm*—Duane Morris, LLP

(57) ABSTRACT

An ophthalmic fluid containing at least one triglyceride, diglyceride, or monoglyceride which is chemically similar or compatible with compounds found naturally in the lipid layer of the tear film of an ocular substrate. Preferably the glycerides are derived from a fatty acid containing at least one unsaturated bond in a cis-configuration in the fatty acid residue. The ophthalmic fluid is arranged in use to provide a protective film across a tear film of an ocular substrate. Furthermore, the ophthalmic fluid is also arranged in use to provide a protective film intermediate a lipid layer of the tear film of the ocular substrate and a contact lens.

5 Claims, No Drawings

OPHTHALMIC FLUID

CROSS-REFERENCE TO RELATED APPLICATIONS

This application is a continuation of U.S. application Ser. No. 10/049,784, filed Feb. 15, 2002 now abandoned, which is the national phase application of PCT/AU00/00977, filed Aug. 16, 2000.

FIELD OF THE INVENTION

The present invention relates to an ophthalmic fluid for improving wear comfort of contact lenses.

BACKGROUND OF THE INVENTION

The tear film, which is the interface between the external environment and the ocular surface has several different functions. It forms a smooth refractive surface over the otherwise irregular corneal surface and lubricates the eyelids. Moreover, it maintains an optimal extracellular environment for epithelial cells of the cornea and conjunctiva where the electrolyte composition, osmolarity, pH, oxygen and carbon dioxide concentrations, nutrient and growth factor concentrations are regulated within narrow limits.

Tears dilute and wash away noxious stimuli. They also provide an antibacterial system for the ocular surface and serve as an entry pathway for polymorphonuclear leukocytes in the case of injury to the ocular surface. As tears have many and varied functions, it is not surprising that they have a complex structure and are produced by several different sources.

The tear film consists of three layers. The inner layer is a mucous layer that coats the cornea and conjunctiva. It was previously thought to be 1 μm, but new evidence suggests that it may be far thicker. The mucous layer consists of mucins, electrolytes, water, IgA, enzymes, glycocalyx, microvilli, immunoglobins, and glycoproteins. The middle layer is an aqueous layer that is about 7 μm thick. This layer contains electrolytes, water, IgA, and proteins, many of which are antibacterial enzymes. Finally, the outer layer is a lipid layer about 0.1 μm thick, which floats on the aqueous layer. The lipid layer contains a complex mixture of hydrocarbons, squalene, wax esters, cholesterol esters, triglycerides, diglycerides, monoglycerides, free fatty acids, free cholesterol, phospholipid, sterol esters, and polar lipids.

Each layer of the tear film is secreted by a different set of orbital glands.

The lipid layer is secreted primarily by the meibomian glands located in the tarsal plates of the lower and upper lids. The glands lie in a row at the edge of the upper and lower eyelids and their ducts open directly onto the inner margin of the eyelids. There are approximately 30 to 40 meibomian glands in the upper lid and 20 to 30 smaller glands in the lower lid. Each gland has an orifice that opens on the lid margin between the tarsal "grey line" and the mucocutaneous junction. The sebaceous glands of Zeis, located at the palpebral margin of the tarsus, and the aprocine glands of Moll, located at the roots of each eyelash, also secrete lipid that is incorporated into the tear film.

Sebum, also called meibum, the meibomian gland secretion, increases the surface tension of the tear film and decreases its rate of evaporation. The evaporation rate of the normal tear film is low because of the protective lipid layer. Approximately 10% to 20% (0.085 μL/minute) of the total tears secreted are lost by evaporation. In the absence of the protective lipid layer, the rate of evaporation is increased 10 to 20 times (1.7 μL/minute).

Meibomian gland secretions contribute to the formation of a stable tear film. Meibomian gland dysfunction may result in dry eye syndrome, keratoconjunctivitis and contact lens intolerance, presumably due to an inadequate or a compromised tear film which is secondary to the meibomian gland dysfunction itself. Meibomian gland dysfunction may be often induced by soft contact lens wear, whilst mebomianitis may result from hard contact lens wear.

There are two major types of dry eye syndromes. Aqueous deficient dry eye syndrome is caused primarily from a lack of tear secretion from the lacrimal gland, whereas evaporative dry eye syndrome is typically caused by lipid insufficiency, a condition related to meibomian gland dysfunction. Both syndromes often co-exist.

It is thought that meibomian gland dysfunction may be caused in response to decreased androgen levels. Human lacrimal glands, meibomian glands and other ocular tissues have androgen receptors. The meibomian gland in particular appears to be a principal target site for androgen activity on the ocular substrate. Androgens appear to stimulate meibomian gland cells to produce lipids which maintains tear film stability and prevent tear film evaporation. Decreased androgen levels frequently occur with fluctuating hormonal changes associated with menopause, pregnancy, lactation and through the use of oral contraceptives. It is also associated with the ageing process in men and women. Auto immune diseases such as Sjörgen's syndrome, rheumatoid arthritis, diabetes, thyroid abnormality, asthma, cataracts, glaucoma and lupus appear to correlate with the presence of meibomian gland dysfunction and evaporative dry eye syndrome.

Certain medications such as antidepressants, decongestants, diuretics, ulcer medication, tranquillisers and beta blockers can also decrease the body's ability to produce lubricating lipids.

Use of antiandrogen medications for prostatic hypertrophy or cancer also appear to correlate with the incidence of meibomian glad dysfunction and evaporative dry eye syndrome.

Evaporative dry eye syndrome may also be caused by environmental conditions such as exposure to smoke, fluorescent lights, air pollution, wind, heaters, air conditioning and dry climates.

Similarly, behavioural patterns, particularly the tendency for VDU users to ignore the normal blinking process, may also interrupt tear production.

Contact lens wearers appear to be particularly susceptible to evaporative dry eye syndrome. Contemporary contact lenses are of two primary types: rigid gas permeable lenses (hard) and hydrogel lenses (soft) comprising between 30% to over 85% water of hydration. Rigid gas permeable lenses are commonly formed from a co-polymer of methylmethacrylate and silicon, termed siloxaneacrylate.

The tear film thickness on the eye is reported to be up to 10 microns, decreasing to 4.5 microns between blinks. The tear film is relatively thin when compared with the thickness of any contact lens, which varies from a minimum of 30 microns to an average of 60–120 microns, and over 250 microns for lenses of considerable optical power. Thus, the sheer mass of any contact lens may compromise the specific functions of the tear film which include the flushing action, the prevention of desiccation of the ocular tissue, the lubrication of the ocular and palpebral surfaces, the formation of an optically smooth curved surface, a vehicle for oxygen and carbon dioxide transport, and the defence of the cornea against trauma, infection or disease. The role of the lipid layer in preventing evaporation is relevant to contact lens wear. If the meibomian glands are obstructed, essentially eliminating the lipid layer, the rate of evaporation dramatically increases by a factor of 10 to 20.

The lipid layer on the surface of all contact lenses is compromised as compared to the lipid layer of the cornea without the contact lenses. A well-fitted contact lens has to rest on a continuous aqueous tear layer sandwiched between the lens and the epithelium, and it has to be coated with a continuous tear film complete with a superficial lipid layer. However, all contemporary contact lenses are unable to mimic the ocular surface properties, and therefore a comparable tear film on the lens surfaces is unable to form.

A lipid layer does not form on hard lenses. There are conflicting reports regarding the presence and/or characteristics of the lipid layer forming on soft lenses. Some claim the complete absence of a lipid layer, while others report it as present but thin, its depth being dependent on the water content of the lens.

Clinical experience indicates that individuals without objective signs of dry eyes or subjective symptoms may experience classical dry eye symptoms while wearing contact lenses. When the contact lens is placed on the eye, the lens alters the normal structure of the tear film and affects its rate of evaporation. It is thought that the lipid layer is compromised causing dehydration of the aqueous layer to accelerate and tears to macerate the skin.

The present invention seeks to overcome at least some of the aforementioned disadvantages

SUMMARY OF THE INVENTION

In accordance with one aspect of the invention there is provided an ophthalmic fluid, wherein the ophthalmic fluid is arranged in use to provide a protective film across a tear film of an ocular substrate, the ophthalmic fluid comprising at least one glyceride of formula (I):

wherein $R^1=R^2=R^3$ is —O—CO—R; or $R^1=R^3$ is O—CO—R when $R^2$ is OH; or $R^1$ is —O—CO—R when $R^2=R^3=$OH; R is a fatty acid residue containing at least one unsaturated bond, and R is the same or different when $R^1=R^3$ or $R^1=R^2=R^3$.

DESCRIPTION OF THE INVENTION

The ophthalmic fluid of the present invention contains at least one triglyceride, diglyceride, or monoglyceride of a fatty acid containing at least one unsaturated bond which is chemically similar to those compounds found naturally in the lipid layer of the tear film of the eye. Alternatively, the ophthalmic fluid of the present invention contains at least one triglyceride, diglyceride, or monoglyceride of a fatty acid containing at least one unsaturated bond which is compatible with those compounds found naturally in the lipid layer of the tear film of the eye. Preferably, the ophthalmic fluid of the present invention contains a compound which biomimics at least one component of the lipid layer of the tear film of the eye. It will also be understood that the ophthalmic fluid may contain mixtures of the abovementioned components. Furthermore, it will also be understood that the fatty acid residues comprised in the diglyceride or triglyceride may be the same or different.

Preferably, the ophthalmic fluid contains at least one triglyceride, diglyceride, or monoglyceride derived from a fatty acid containing at least one unsaturated bond in a cis-configuration in the fatty acid residue. However, glycerides derived from a fatty acid containing at least one unsaturated bond in a trans-configuration in the fatty acid residue may also be suitable. It is envisaged that the carbon chain length of the fatty acid residue will range from. 16 carbon to 20 carbon atoms. However, the carbon chain length may vary from that provided that the melting point of the triglyceride, diglyceride or monoglyceride is sufficiently low for handling and application purposes. Preferably, the ophthalmic fluid contains at least one triglyceride, diglyceride or monoglyceride derived from oleic acid, linoleic acid, linolenic acid, palmitoleic acid, arachidonic acid, or mixtures thereof While it is possible for the fatty acid of the glyceride of formula (I) to be administered alone, it is also possible to topically apply the glyceride of the present invention to the ocular substrate as a pharmaceutical composition. The pharmaceutical composition of the present invention comprises at least one glyceride, as defined above, in admixture with one or more suitable carriers or diluents therefor and optionally other therapeutic ingredients. The carrier(s) and diluent(s) must be "suitable" in the sense of being compatible with the other components of the formulation and not deleterious to the recipient thereof.

Naturally occurring vegetable oils, such as grapeseed oil, having glycerides derived from linoleic acid may also be used as an ophthalmic fluid in accordance with the present invention, particularly if the physical properties of such an oil is to form oily droplets which will coat the inner surface of the contact lens, and the chemical properties of the components of said oil are such as to be superficially recognised by the ocular substrate as components of the lipid layer of the tear film of the eye.

Glycerides characteristically form oily droplets. Upon application of the ophthalmic fluid of the present invention to an inner surface of the contact lens, the glyceride molecules bond together to form a glyceride film which coats the inner surface of the contact lens.

The glyceride film has two purposes, one of which is to mask the foreign nature of the contact lens from the ocular substrate. The glyceride film is comprised of glycerides which are chemically similar to those compounds found naturally in the lipid layer of the tear film of the eye. In this way, the coated contact lens is superficially recognised by the ocular substrate as a substance that is naturally produced by the eye. Irritation arising from rejection of an alien substance in the eye is subsequently reduced.

The purpose of the lipid layer of the tear film is to provide an effective barrier against tear loss by dehydration and maceration. When the lipid layer is compromised upon application of the contact lens to the ocular substrate, the rate of evaporation from the tear film increases. The contact lens wearer consequently experiences discomfort and dry eye syndrome symptoms. The second purpose of the glyceride film on the inner surface of the contact lens is thus to reinforce the lipid layer of the tear film. The compromised lipid layer is effectively rebuilt or reinforced by the application of a glyceride film comprised of substances which are naturally produced and secreted by the eye to form the lipid layer in the tear film.

The resulting reduction in tear loss and minimisation of lipid layer disintegration is noticed by the eye as a reduction of the irritation usually associated with the application of contact lenses. Hence, the contact lens wearer experiences increased wear comfort.

The ophthalmic fluid of the present invention is suitable for use with gas permeable (hard) contact lenses or hydrogel (soft) contact lenses. In use, 2–3 drops of the ophthalmic fluid of the present invention are placed onto the inside surface of the contact lens. The ophthalmic fluid is then distributed to cover fully and evenly the inside surface of the contact lens by rubbing the ophthalmic fluid into the lens with a fingertip or any other suitable applicator. It is envisaged that the ophthalmic fluid will be biologically sterile.

The lipid layer of the tear film is also compromised in subjects who experience dry eye syndrome and meibomian gland dysfunction. The ophthalmic fluid of the present invention acts to reinforce the lipid layer of the tear film because its components are either chemically similar to, chemically and/or biologically compatible with, or biomimic at least one component naturally occurring in the lipid layer of the tear film. Thus the ophthalmic fluid of the present invention is suitable for the preparation of medicaments for the prevention and treatment of dry eye syndrome. The ophthalmic fluid of the present invention is suitable for the preparation of medicaments for the treatment of meibomian gland dysfuntion.

The present invention is further illustrated by the following examples.

The inside of a contact lens was coated with 2–3 drops of the ophthalmic fluid of the present invention and fitted to the subject in the conventional manner. The subject reported on the perceived ease of inserting the coated lens, the subject's sensual reaction to the coated lens and the resulting vision through the coated lens, in relation to hard and soft contact lenses.

EXAMPLE 1

Triolein(1,2,3-tri(cis-9-octadecenoyl)glycerol) (Sigma Chemicals, 99%)

The subject reported that a gas permeable (hard) lens coated with triolein was very comfortable to insert, the edges of the lens seemingly smoothed out so as to reduce, but not totally eliminate, the normal discomfort associated when inserting a hard lens. Once inserted, the subject could not feel the presence of the coated lens. The subject's vision through the coated lens was excessively and persistently blurred. Excess triglyceride did not drain into the lacrimal ducts, and had to be physically removed.

The subject reported that a hydrogel (soft) lens coated with triolein was very difficult to insert and did not noticeably ameliorate the normal discomfort associated when inserting a soft lens. The subject's vision through the coated lens was clear.

EXAMPLE 2

Trilinolein(1,2,3-tri(cis, cis-9,12octadecadienoyl)glycerol) (Sigma Chemicals, 99%)

The subject reported that a gas permeable (hard) lens coated with trilinolein was very comfortable to insert. In comparison to a hard lens coated with triolein, however, the sensation caused by the edges of the lens on the eye was not reduced to the same extent by a hard lens coated in trilinolein. Once inserted, the subject could not feel the presence of the coated lens. The subject initially experienced blurred vision which cleared after approximately 60 seconds. Excess triglyceride drained into the lacrimal ducts, and a residue did not remain on the eye surface or eyelid. The subject reported no tear expulsion.

The subject reported that a hydrogel (soft) lens coated with trilinolein was easy to insert, and produced a noticeable amelioration of the normal discomfort associated when inserting a soft lens. Once inserted, the subject could not feel the presence of the coated lens. The subject's vision through the coated lens was immediately clear. Excess triglyceride drained into the lacrimal ducts, and a residue did not remain on the eye surface or eyelid. The subject reported no tear expulsion.

EXAMPLE 3

Tripalmitolein(1,2,3-tri(cis-9-hexadecenoyl)glycerol) (Sigma Chemicals, 98%)

The subject reported that a gas permeable (hard) lens coated with tripalmitolein was very comfortable to insert. In comparison to a hard lens coated with triolein, however, the sensation caused by the edges of the lens on the eye was not reduced to the same extent by a hard lens coated in tripalmitolein. Once inserted, the subject could not feel the presence of the coated lens. The subject's vision through the coated lens was excessively blurred. Excess tripalmitolein did not drain into the lacrimal ducts, and had to be physically removed.

The subject reported that a hydrogel (soft) lens coated with tripalmitolein was very difficult to insert as the lens was more adhesive to a finger coated with the fluid than to the actual ocular substrate. However, once the lens was inserted onto the eye, the subject found the soft lens coated with tripalmitolein to be comfortable. The subject's vision through the coated lens was blurred.

EXAMPLE 4

Trilinolenin(1,2,3-tri(cis, cis, cis -9,12,15-octadecatrienoyl)glycerol) (Sigma Chemicals, 98%)

The subject reported that although a gas permeable (hard) lens coated with trilinolenin was easy to insert, the subject experienced extreme irritation with increased tear production and maceration of the ocular substrate. The subject's vision through the coated lens was blurred.

The subject reported that a hydrogel (soft) lens coated with trilinolenin was difficult to insert, the lens becoming quite greasy to handle. However, once the soft lens coated with trilinolenin was inserted onto the ocular substrate, the coated lens was comfortable to wear. The subject initially experienced blurred vision which cleared after 2 minutes.

EXAMPLE 5

Triarachidonin(1,2,3-tri(cis, cis, cis, cis, -5,8,11,14 -eicosatetraenoyl)glycerol) (Sigma Chemicals, 98%)

The subject reported that a gas permeable (hard) lens coated with triarachidonin was easy to insert with no residual greasy feel. Once inserted, the coated lens was comfortable to wear. The subject did not experience tear production or maceration. The subject's vision through the coated lens was excessively and persistently blurred. The subject reported that a hydrogel (soft) lens coated with triarachidonin was easy to insert with no residual greasy feel. However, a soft lens coated with triarachidonin did not produce any noticeable improvement in the wearer's comfort. The subject experienced increased tear production upon insertion of the soft lens, but no maceration. The subject had clear vision.

The subject noticed that the soft lens became cloudy or frosty in appearance upon application of triarachidonin onto its surface.

EXAMPLE 6

| Safflower Oil (Melrose, organic unrefined, cold pressed). | | |
|---|---|---|
| Composition: | | (per 100 g) |
| Saturates | Palmitic | 7 g |
| | Stearic | 2 g |
| Monounsaturates | Oleic | 12 g |
| Polyunsaturates | Linoleic | 78 g |

The subject reported that a gas permeable (hard) lens coated with safflower oil was difficult to insert with a distinct residual greasy feel. The subject experienced a painful stinging sensation upon insertion of the coated lens onto the ocular substrate combined with maceration. The subject's vision through the coated lens was excessively and persistently blurred.

The subject reported that a hydrogel (soft) lens coated with safflower oil was difficult to insert, the lens becoming quite greasy to handle. The subject experienced a painful stinging sensation upon insertion of the coated lens onto the ocular substrate. The subject's vision through the coated lens was blurred. The excess oil did not drain into the lacrimal ducts, and had to be physically removed

EXAMPLE 7

| Walnut Oil (Anglia Oils Ltd). | | |
|---|---|---|
| Composition: | | |
| Saturates | Palmitic | 8–11% |
| Monounsaturates | Oleic | 15–18% |
| Polyunsaturates | Linoleic | 51–62% |
| | Linolenic | 10–19% |

The subject reported that a gas permeable (hard) lens coated with walnut oil was difficult to insert with a distinct residual greasy feel. The coated lens was comfortable to wear, the only discomfort arising from the edges of the lens. The subject's vision through the coated lens was persistently blurred.

The subject reported that a hydrogel (soft) lens coated with walnut oil was difficult to insert, the lens becoming quite greasy to handle. The subject experienced a painful persistent irritation upon insertion of the coated lens onto the ocular substrate. The coated lens also produced excessive tear production. The subject's vision through the coated lens was blurred. The excess oil did not drain into the lacrimal ducts, and had to be physically removed

EXAMPLE 8

| Canola Oil (Melrose, organic unrefined). | | |
|---|---|---|
| Composition: | | (per 100 g) |
| Saturates | Palmitic | 7.0 g |
| | Stearic | 7.0 g |
| Monounsaturates | Undetermined | 64.0 g |
| Polyunsaturates | Linoleic | 19.5 g |
| | Linolenic | 9.5 g |

The subject reported that a gas permeable (hard) lens coated with canola oil was difficult to insert with a distinct residual greasy feel. The subject experienced extreme discomfort and irritation upon insertion of the coated lens onto the ocular substrate combined with maceration and excessive tear production. The subject's vision through the coated lens was excessively and persistently blurred.

The subject reported that a hydrogel (soft) lens coated with canola oil was difficult to insert, the lens becoming quite greasy to handle. The subject experienced a painful stinging sensation upon insertion of the coated lens onto the ocular substrate, combined with maceration and excessive tear production. The subject's vision through the coated lens was blurred.

EXAMPLE 9

| Grapeseed Oil (Aurora). | | |
|---|---|---|
| Composition: | | |
| Saturates | Undetermined | 7–8% |
| Monounsaturates | | trace |
| Polyunsaturates | Linoleic | 72–75% |
| | Linolenic | trace |

The subject reported that a gas permeable (hard) lens coated with grapeseed oil was easy to insert and comfortable to wear. The subject noticed slight discomfort associated with the edges of the lens on the eye which was not reduced to the same extent as with a hard lens coated with triolein. The subject initially experienced blurred vision which cleared after approximately 30 seconds. An oily residue did not remain on the eye surface or eyelid. The subject reported no tear expulsion.

The subject reported that a hydropel (soft) lens coated with grapeseed oil was easy to insert, and produced a noticeable amelioration of the normal discomfort associated when inserting a soft lens. Once inserted, the subject could not feel the presence of the coated lens. The subject's vision through the coated lens was initially blurred, but cleared after 30 seconds.

Excess grapeseed oil drained into the lacrimal ducts, and a residue did not remain on the eye surface or eyelid. The subject reported no tear expulsion or maceration. In light of the results of Examples 1 to 9, it is envisaged than the ophthalmic fluid of the present invention may contain a glyceride derived from oleic acid in combination with a glyceride derived from linoleic acid. The glyceride derived from oleic acid imparts a character to the ophthalmic fluid in which the edges of a hard lens are seemingly smoothed out so as to reduce the normal discomfort associated when inserting a hard lens, whilst the glyceride derived from linoleic acid provides improved wear comfort and clear vision through the lens.

Modifications and variations as would be apparent to a skilled addressee are deemed to be within the scope of the present invention.

What is claimed is:

1. A method of providing a protective film intermediate a lipid layer of a tear film of an ocular substrate and a contact lens, comprising topically applying to an inner surface of the contact lens a coat of an ophthalmic fluid and subsequently applying the coated inner surface of the contact lens to the ocular substrate, wherein the ophthalmic fluid consists essentially of at least one glyceride of formula (I):

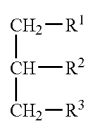
(I)

wherein $R^1=R^2=R^3$ is O—CO—R; or $R^1=R^3$ is O—CO—R when $R^2$ is OH; or $R^1$ is O—CO—R when $R^2=R^3=$OH; R is a fatty acid residue comprising 16–20 carbon atoms and containing at least one unsaturated bond, and R is the same or different when $R^1=R^3$ or $R^1=R^2=R^3$.

2. The method according to claim 1, characterized in that irritation to the ocular substrate associated with the application of the contact lens to the ocular substrate is reduced.

3. The method according to claim 1, characterized in that the method reinforces the lipid layer of the tear film of the ocular substrate upon application of the contact lens to the ocular substrate.

4. The method according to claim 1, characterized in that the fatty acid residue contains at least one unsaturated bond in a cis-configuration.

5. The method according to claim 1, characterized in that the ophthalmic fluid contains at least one triglyceride, diglyceride, or monoglyceride derived from linoleic acid, linolenic acid, palmitoleic acid, arachidonic acid, oleic acid or mixtures thereof.

* * * * *